United States Patent [19]

Staunton

[11] 4,066,365
[45] Jan. 3, 1978

[54] TEMPERATURE CONTROL APPARATUS
[75] Inventor: John J. J. Staunton, Oak Park, Ill.
[73] Assignee: The Perkin-Elmer Corporation, Norwalk, Conn.
[21] Appl. No.: 690,891
[22] Filed: May 28, 1976
[51] Int. Cl.² ............ G01N 21/16; F25B 21/02
[52] U.S. Cl. ............................. 356/244; 62/3; 350/93; 356/96; 356/246
[58] Field of Search ............ 356/244, 246, 96; 62/3; 350/93, 86

[56] References Cited
FOREIGN PATENT DOCUMENTS
884,570  12/1961  United Kingdom ............ 350/86

Primary Examiner—Vincent P. McGraw
Attorney, Agent, or Firm—S. A. Giarratana; F. L. Masselle

[57] ABSTRACT

Control of test chambers or specimens to stabilized temperatures at set points over a wide temperature range is accomplished with improved response time by an arrangement of cascaded Peltier affect heat pumps. Generally, power to a first Peltier unit in the arrangement is controlled relatively to the temperature deviation of the specimen from the desired set point, while power to a second Peltier unit therein is controlled proportionally to the temperature differential across the first Peltier unit. In applicatons where large thermal losses to ambient occur, a portion of the power control signal to the second Peltier unit is applied to offset the temperature set point as a compensation for such losses. Improvement in approach to stabilized temperature is further attained by applying an anticipation signal in proportion to the temperature gradient between the specimen and the first Peltier unit to decrease the monitored deviation of the specimen temperature from the set point. For system protection the power control signals to the Peltier units are shut off to preclude thermal runaway in applications where the specimen temperature is monitored by a sensor which must be exposed to ambient conditions during set-up periods.

9 Claims, 7 Drawing Figures

TEMPERATURE CONTROL APPARATUS

BACKGROUND OF THE INVENTION

The present invention relates to temperature control apparatus which includes cascaded Peltier units, especially such apparatus wherein the Peltiers are controlled for improved thermal response time to stabilize specimen temperatures at set points over a wide temperature range. Temperature control apparatus must be included in analytical instruments when the analyzed parameter varies with the temperature of the test specimen. Although the range over which the specimen temperature must be varied by such control apparatus depends on the particular type of analysis, the analytical capability of instruments is limited by the temperature control apparatus where rapid analysis is required over a wide temperature range or where a great number of specimens must be individually analyzed in minimized time durations.

Use of the thermoelectric module or Peltier unit to both supply and remove heat has revolutionized the art of temperature control apparatus in analytical instruments by doing away with the circulating water baths that were previously necessary. However, thermal lags existing between the test specimen and the Peltier units in state of the art temperature control apparatus greatly limit the capability of analytical instruments because the thermal response time for arriving at a temperature set point can only be improved by increasing the temperature gradient to reduce these thermal lags, but when the temperature set point is reached an overshoot then occurs in proportion to the temperature gradient imposed to reach that set point. Although cascaded Peltier arrangements are commonly known in which the overall thermal difference is broken up into segments, the temperature gradient across each segment is often derived from structural characteristics or from fixed temperature set points in all such arrangements. Therefore, a compromise must be made as to the temperature gradient that acts against the thermal lag of each segment and the minimum temperature stabilization response time is limited by this compromise.

SUMMARY OF THE INVENTION

It is the general object of the present invention to provide temperature control apparatus including cascaded Peltier units which are controlled to improve thermal response time in reaching stabilized temperatures at set points over a wide temperature range.

It is another object of the present invention to control the Peltier units in at least one thermal cascade segment thereof proportionally to the temperature differential across another thermal cascade segment thereof, to thereby reduce the effect of thermal lag across the latter segment on the temperature stabilization response time.

It is still another object of the present invention to control the Peltier units in at least one thermal cascade segment thereof proportionally to the temperature deviation of the specimen from a set point which is offset proportionally to the temperature differential across the same thermal cascade segment, to thereby compensate for thermal losses to ambient.

It is a further object of the present invention to control the Peltier units thereof so that thermal runaway is precluded when the sensor monitoring specimen temperature is exposed to ambient conditions throughout setup periods.

It is still a further object of the present invention to provide anticipation control therein over the thermal transfer between the specimen and one thermal cascade stage by utilizing the temperature differential therebetween to offset the monitored specimen temperature toward the set point.

These objects are accomplished in one embodiment of the present invention by thermally connecting two Peltier units in series, with power to the first Peltier unit being controlled in relation to the temperature deviation of the specimen from the desired set point and with power to the second Peltier unit being controlled in proportion to the temperature differential across the first Peltier unit. Thermal losses to ambient are compensated by applying a portion of the power control signal for the second Peltier unit to offset the temperature set point. Thermistors are utilized in a constant sensitivity bridge circuit to derive the temperature differential across the first Peltier unit, and the overall voltage applied to the bridge provides a convenient voltage threshold at which the Peltier units are shut off to preclude thermal runaway when the specimen temperature sensor is exposed to ambient conditions. Furthermore, an additional thermistor is utilized in this bridge circuit to derive the anticipation control signal by which the monitored specimen temperature is offset toward the set point proportionally to the temperature gradient between the specimen and the first Peltier.

BRIEF DESCRIPTION OF THE DRAWINGS

The manner in which these and other objects of the present invention are achieved will be best understood by reference to the following description, the appended claims, and the attached drawings wherein:

DESCRIPTION OF THE PREFERRED EMBODIMENTS

Figure 1:
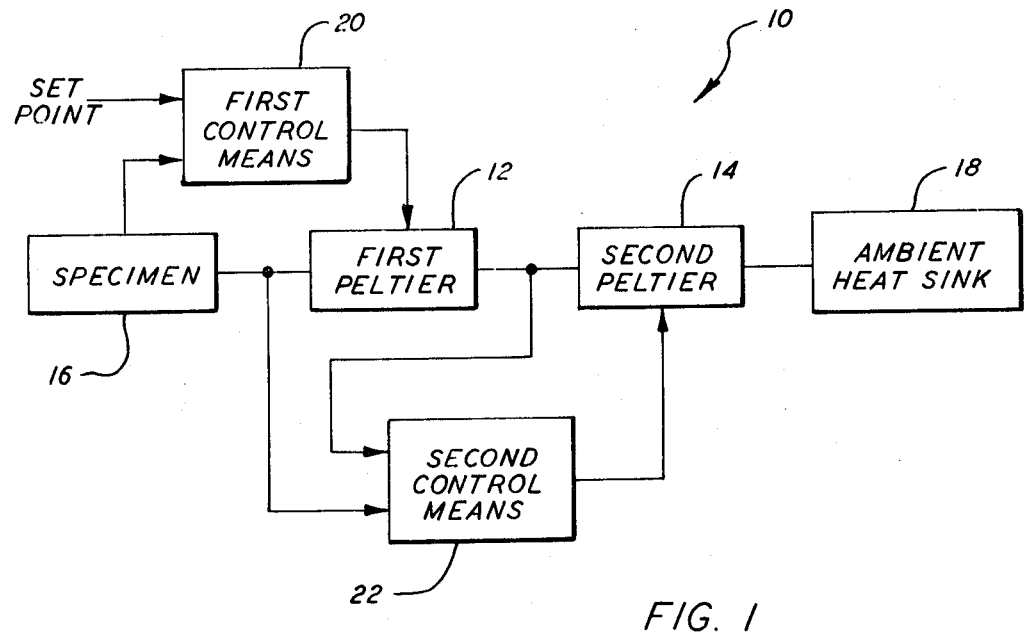
FIG. 1 is a block diagram relating to the temperature control apparatus of this invention.

Turning now to the drawings, the block diagram of FIG. 1 relates to the temperature control apparatus 10 of this invention wherein stabilization at set point temperatures are rapidly attained over a wide temperature range. In apparatus 10, Peltier units 12 and 14 are disposed within a cascade arrangement to control thermal transfer between a specimen 16 and an ambient heat sink 18. Peltier units are electrical heat pumps across which thermal transfer in either direction is possible depending on the polarity of the control signal thereto. Thermal transfer across Peltier unit 12 is regulated by a means 20 for controlling the power thereto according to the temperature differential between the specimen and a set point, while thermal transfer across Peltier unit 14 is regulated by a means 22 for controlling the power thereto proportionally to the temperature differential across Peltier unit 12.

Peltier unit 12 approaches shut-off as the specimen temperature approaches the set point, whereas Peltier unit 14 approaches shut-off as the temperature differential across Peltier 12 approaches zero. When the set point is reached any overshoot occurring due to the thermal lag between Peltier 12 and specimen 16 will cause reversal of Peltier unit 12 by the control means 20. Furthermore, this reversal will quickly cause reversal of Peltier unit 4 through means 22 so that the overshoot which does occur is considerably reduced in comparison to prior art cascade Peltier arrangements. Because the apparatus 10 of this invention reduces both the overshoot at set point and the thermal oscillations thereabout to settle the overshoot, stabilized specimen temperature at set points are reached in low response times over a wide temperature range. Of course, those skilled in the art will appreciate that any number of Peltier units greater than one could be cascaded in the temperature control apparatus 10 of this invention or that any number of Peltier units could be utilized in each cascade segment thereof. Artisans will also appreciate that the power rating of the Peltier units in each cascade segment will depend on the particular application to which the invention is applied.

Figure 2:
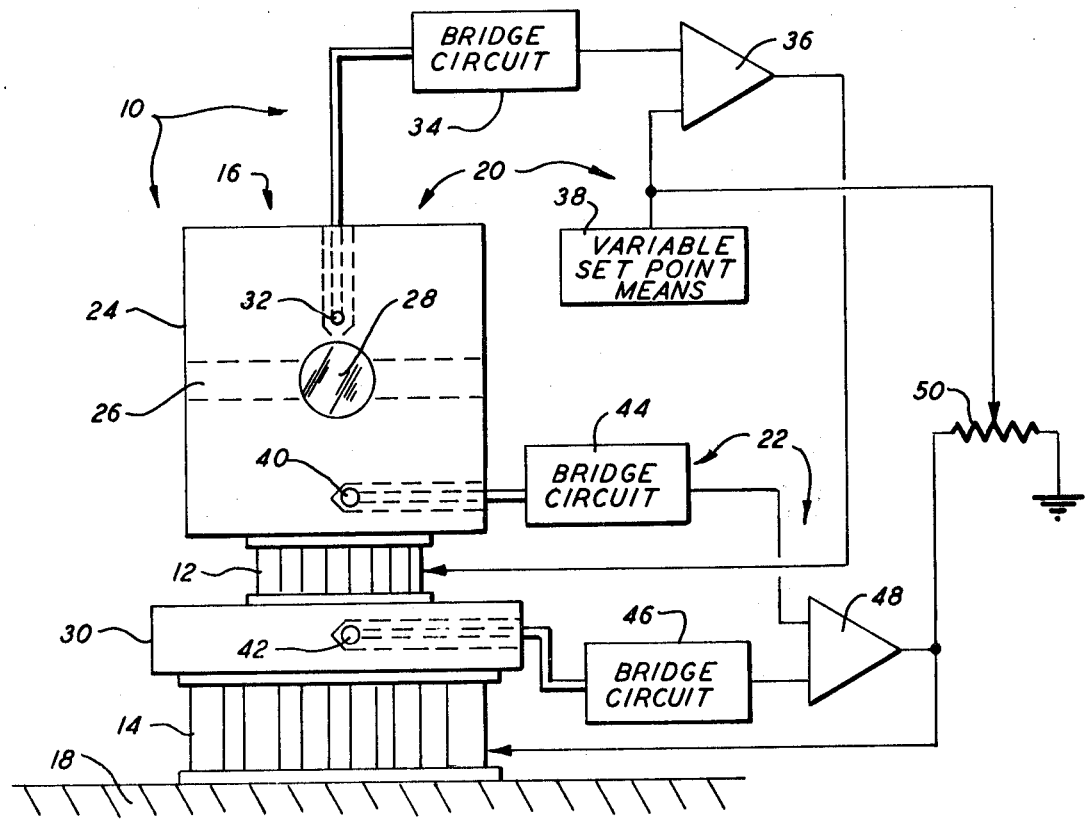
FIG. 2 illustrates one specific embodiment of this invention wherein the temperature of a flow cell within a spectrophotometer is controlled.

Although many applications exist in analytical instruments for the temperature control apparatus 10 of this invention, for brevity only embodiments thereof which apply to temperature control of specimen cells in spectrophotometers will be disclosed hereinafter. The first such embodiment is illustrated in FIG. 2 where the block elements of FIG. 1 are identified by the same reference numerals. In this embodiment, the specimen 16 is a flow cell into which the sample for spectrophotometer analysis is aspirated and the ambient heat sink 18 is the frame of the spectrophotometer or some other heat sink of substantially constant temperature. Of course, the temperature control apparatus 10 of this invention is incorporated in this embodiment to regulate thermal transfer between the sample in the flow cell 16 and the ambient heat sink 18. The flow cell 16 is a block 24 of high thermal conductivity material, with a passage 26 therethrough and with windows 28 aligned on an axis transverse to passage 26 to pass the radiation beam through the sample for analytical purposes. In this embodiment, a transfer heat sink 30 is disposed to interface between one thermal junction on each of the Peltier units 12 and 14, while the other thermal junction of the Peltier unit 12 is interfaced directly with the block 24 and the other thermal junction of the Peltier unit 14 is interfaced directly with the ambient heat sink 18. The power control means 20 for Peltier unit 12 includes a temperature sensor 32 which is thermally disposed in the block 24 and electrically disposed in a suitable bridge circuit 34 from which the output is connected to one input of a comparator 36. A means 38 for establishing a variable set point is connected to the other input of the comparator 36 and the output therefrom is connected to control the thermal transfer across Peltier unit 12. The power control means 22 for Peltier unit 14 includes temperature sensors 40 and 42 which are thermally disposed separately in the block 24 and the transfer heat sink 30 respectively, and electrically disposed respectively in suitable bridge circuits 44 and 46 from which the outputs thereof are separately connected to the inputs of a comparator 48. Output from the comparator 48 is connected to control the thermal transfer across Peltier unit 14. Temperature sensor 32 is disposed adjacent to the sample flow passage 26, while temperature sensors 40 and 42 are disposed adjacent to the thermal junctions of the Peltier unit 12, so that thermal lags are avoided where possible.

Thermal transfer to raise or lower the sample in the flow cell 16 to a desired temperature is accomplished through the block 24 for which such design parameters as specific heat, thermal conductivity and configuration must be given due consideration so that the merits of this invention will not be frustrated. As a result, the sample is maintained substantially at the temperature set point of the power control means 20 which regulates the thermal transfer between the Peltier unit 12 and the block 24. The thermal response time required for the sample in the flow cell 16 to stabilize at any set point over a wide temperature range is low by comparison to prior art cascaded Peltier arrangements for the same reasons discussed previously in regard to FIG. 1.

Even when insulation is utilized for inhibiting thermal losses to ambient, such losses are always present to some degree as long as a temperature differential exists relative to ambient. The temperature control apparatus 10 of FIG. 2 will maintain the sample in the flow cell 16 at the temperature set point while thermal losses to ambient of moderate magnitudes occur. However, where the temperature differential relative to ambient is very large and/or no insulation can be used, a portion of the output fro comparator 48 may be applied to offset the temperature set point at the input of comparator 36 to compensate for thermal losses to ambient. To give the proper correction the output from comparator 48 must be substantially proportional to the temperature differential across Peltier unit 12 and independent of the average temperature of said unit. This compensation is only applied to the degree that the thermal losses to ambient are sufficient to affect that temperature differential. The output from comparator 48 is grounded through a potentiometer 50 on which the wiper is connected to offset the temperature set point at the input of comparator 36 and therefore, the degree of compensation is variable.

Figure 3:
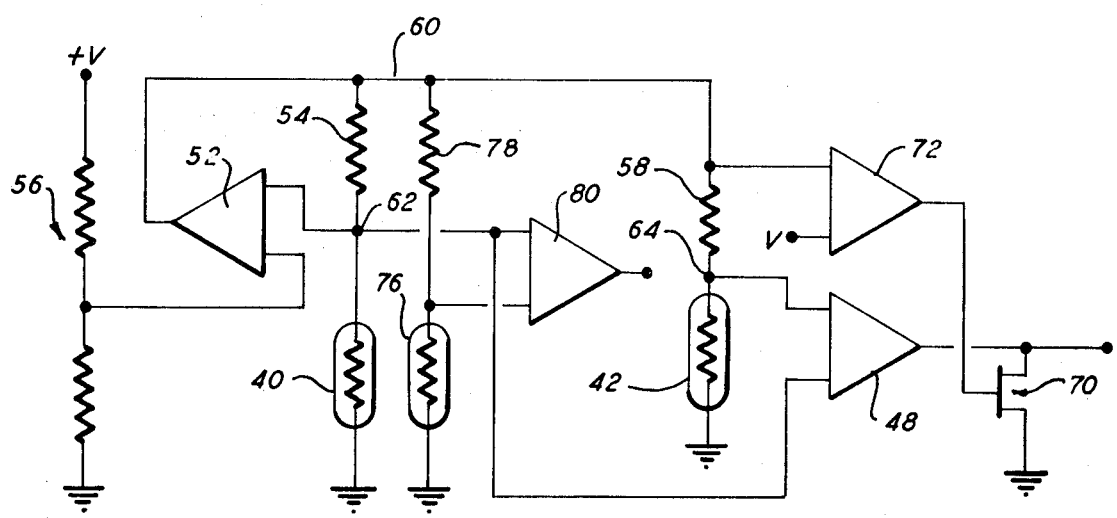
FIG. 3 is the schematic diagram for the constant sensitivity bridge circuit which may be used in the apparatus of this invention.

In practice any type of temperature sensors having suitable sensitivity may be utilized in the temperature control apparatus 10 of this invention and the bridge circuits thereof must be suitable to provide voltage signals that are proportional to the temperatures monitored by these sensors. Where thermistors are utilized to monitor the differential temperature across Peltier unit 12, bridge circuits 44 and 46 can be combined into a single bridge circuit as shown in FIG. 3. Because the response of thermistors to temperature is characteristically nonlinear, this bridge circuit is linearized, i.e., made to have a substantially constant sensitivity, by including an operational amplifier 52 which is connected differentially with the output therefrom fed back to drive the bridge at circuit point 60. Resistor 54 and thermistor 40 establish a voltage at point 62 in one leg of the bridge connected to one input of amplifier 52; the other input thereof is connected to the tap point on a voltage divider 56. Another resistor 58 is connected to resistor 54 at the output of operational amplifier 52 at bridge circuit point 60. Thermistor 42 is connected to the other side of resistor 58 to thereby establish bridge circuit point 64 and the thermistors 40 and 42 are interconnected through ground to complete the bridge circuit.

Because of the closed loop around operational amplifier 52, the inputs thereof are at substantially at the same voltage levels with no current flowing into either of these inputs. Therefore, the voltage at bridge circuit point 62 remains substantially constant as the resistance of thermistor 40 changes with temperature so that the current flowing through this thermistor is low when the resistance of the thermistor is high. Since the current flowing through thermistor 40 must also flow through resistor 54, the voltage at bridge circuit point 60 must vary in direct proportion to the resistance of thermistor 40 and hence changes as a function of the temperature. Consequently, the current flowing through thermistor 42 is also low when the resistance of thermistor 40 is high and the bridge circuitry provides substantially constant sensitivity in that the voltage per degree temperature differential between the thermistors 40 and 42 is the difference of two IR drops, both of which are controlled to stay within the same narrow range of magnitude. Comparator 48, then, may have one input connected to circuit point 64, while the other input may be connected to circuit point 62 or an equivalent constant voltage, so that the output of comparator 48 is a substantially constant linear function of the temperature difference between thermistors 40 and 42 at any temperature of thermistor 40 over a design range.

Figure 4:
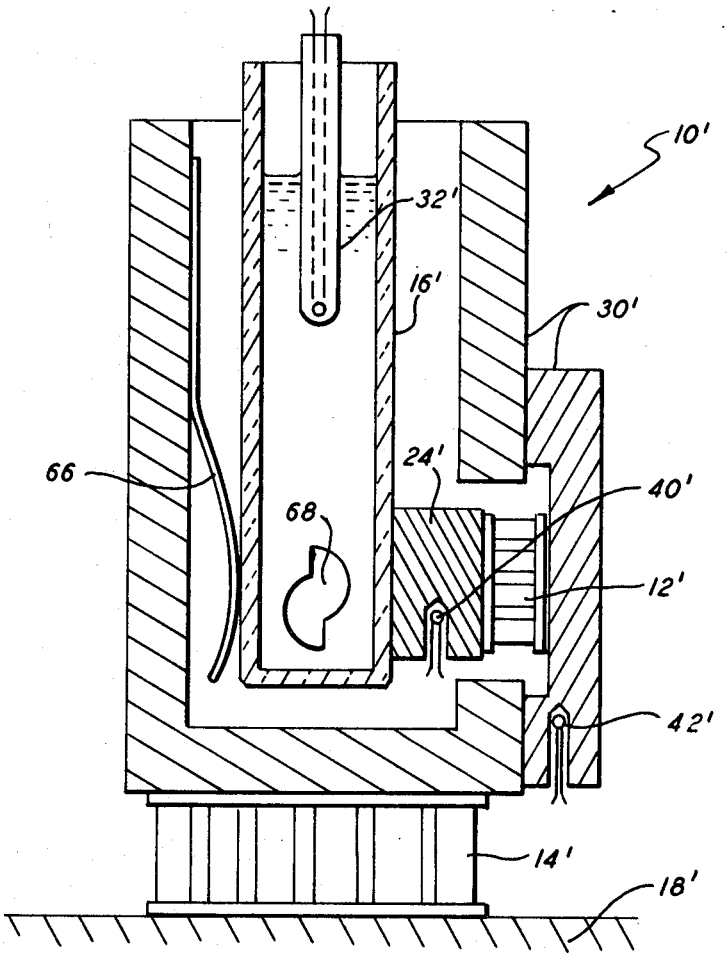
FIG. 4 illustrates another specific embodiment of this invention wherein the temperature of a cuvette within a spectrophotometer is controlled.

Another embodiment of this invention as applied to the art of spectrophotometers is shown in FIG. 4 where, because of the similarities that exist with the apparatus of FIG. 2 similar components are designated with the same reference numerals as those used in FIG. 2, except that a prime (') is added thereto. In this embodiment, the specimen 16' is a cuvette having glass or silica walls and containing samples for spectrophotometer analysis. The ambient heat sink 18' is again the frame of the spectrophotometer or some other heat sink of substantially constant temperature. Thermal transfer to the cuvette 16' is made through a thermal contact bar 24' which is analogous to the block 24 in FIG. 2. Peltier 12' interfaces between the thermal contact bar 24' and a cuvette basket 30' which is analogous to the transfer heat sink 30 in FIG. 2. A spring 66 of low thermal conductivity is affixed on the cuvette basket 30' to hold the cuvette 16' against the thermal contact bar 24' and Peltier 14' interfaces between the cuvette basket 30' and the ambient heat sink 18'. An agitator 68 may be disposed within the cuvette 16' to stir the sample continuously and temperature sensor 32' is disposed within a sheath which is immersed into the sample. Temperature sensors 40' and 42' are disposed across the Peltier 12' in the thermal contact bar 24' and the cuvette basket 30' respectively. Peltiers 12' and 14' are controlled as described and explained previously for the temperature control apparatus 10 of FIG. 2, and thermistors 40' and 42' may be disposed in the constant sensitivity bridge circuitry of FIG. 3.

It should be recognized without further explanation by those skilled in the art that cuvette basket 30' and the thermal contact bar 24' could be extended along an axis perpendicular to the plane of FIG. 4 in providing for a plurality of cuvettes 16'. Of course, the thermal contact bar 24' would interface with each such cuvette 16' and the temperature sensor 32' would be disposed in the thermally centered cuvette 16'. Because thermal lag in the contact bar will limit the speed and accuracy of equilibration attainable with the apparatus of this invention, high thermal conductivity and low thermal storage capacity is exceptionally important in this member. At any location where thermal transfer occurs by conduction through a material, the thermal storage capacity is determined by the material's specific heat. Therefore a possible improvement over a metal bar is afforded by a heat pipe wherein thermal transfer occurs through vapor convection. Heat pipes in the art to be of low thermal storage capacity. Conventionally within heat pipes, thermal transfer is made between two walls by the vapor of a liquid without changing the temperature of the liquid. The vapor condenses on the wall being heated and a wicking system returns the condensate to the other wall where vaporization takes place. For spectrophotometer applications, a 0°–100° C working temperature range is usual for the thermal contact bar 24' in the FIG. 4 embodiment and methanol would be a suitable liquid for a heat pipe used in such an application. As compared to the use of solid copper for the thermal contact bar 24' in that application, a reduction in thermal storage capacity of over 80% can be realized from the use of a heat pipe.

When it becomes necessary to change the sample in the cuvette 16' of the FIG. 4 embodiment, the temperature sensor 32' must be removed therefrom for some period of time. Because during this period of time the temperature sensor 32' is exposed to ambient conditions rather than to the sample temperature it is probable that control of the Peltier units 12' and 14' will be lost to cause a condition of thermal runaway. To prevent failure of either Peltier unit 12' or 14' which could result from thermal runaway, a single direction safety shut-off feature for Peltier 12' is included in the circuitry of FIG. 3. The gate of an FET switch 70 is connected to the output from a comparator 72, with the FET switch 70 being connected to ground the output from comparator 48. The inputs to the comparator 72 are connected to the bridge circuit point 60 and a d.c. voltage reference respectively. As discussed previously, the voltage at bridge circuit point 60 varies as a function of the temperature of thermistor 40 and therefore, this voltage can be used to measure the temperature of Peltier 12'. The voltage reference at the input to comparator 72 can be set so that before a destructive temperature is reached, output from comparator 72 renders FET switch 70 conductive to ground out the control signal of Peltier 12'. When Peltier 12' is shut off, input to Peltier 14' will also be shut down since Peltier 14' is controlled by the heat pumping rate of Peltier 12'.

Figure 5:
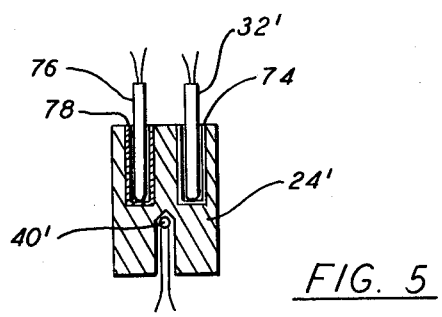
FIG. 5 illustrates a further embodiment of this invention wherein the temperature of a cuvette within a spectrophotometer is controlled.

Because the wall of the cuvette 16' in FIG. 4 presents an undesirable thermal lag, another embodiment of this invention is shown in FIG. 5. As many similarities exist between the apparatus of FIG. 4 and that of FIG. 5, similar components are designated in FIG. 5 with the same reference numerals as those used in FIG. 4 but with a double prime (") added thereto. In this embodiment, and extending portion is disposed on the thermal contact bar 24" and is immersed into the sample within the cuvette 16" from above the cuvette basket 30". The temperature sensor 32" is adjacently disposed to the sample within the extending portion of the thermal contact bar 24" and the agitator 68" is again disposed within the cuvette 16" to stir the sample continuously. As before, Peltier unit 12" interfaces between the thermal contact bar 24" and the cuvette basket 30", while Peltier unit 14" interfaces between the cuvette basket 30" and the ambient heat sink 18". Temperature sensors 40" and 42" are again disposed across the Peltier unit 12" in the thermal contact bar 24" and the cuvette basket 30" respectively. Otherwise, Peltier units 12" and 14" are controlled as described and explained previously for the temperature control apparatus 10 of FIG. 2, and thermistors 40" and 42" may be disposed in the constant sensitivity bridge circuit of FIG. 3.

Figure 6:
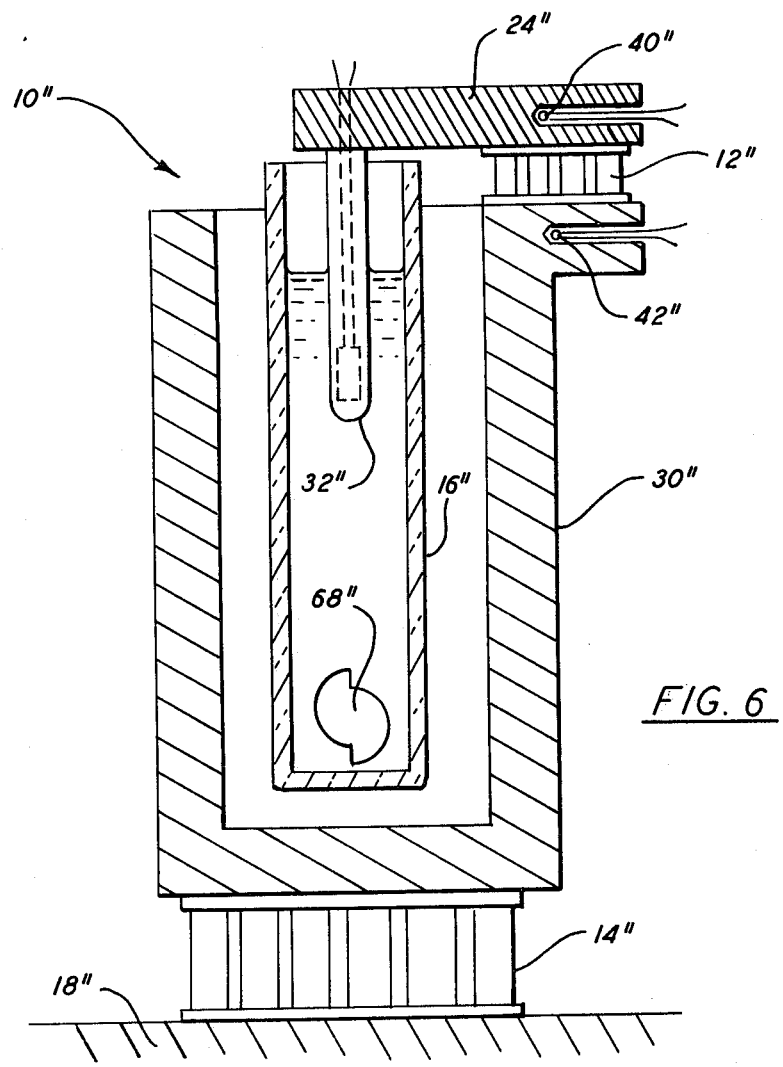
FIG. 6 illustrates the modifications that are possible in the thermal contact bar of FIG. 4 to permanently accommodate temperature sensors in still another specific embodiment of this invention.
Figure 7:
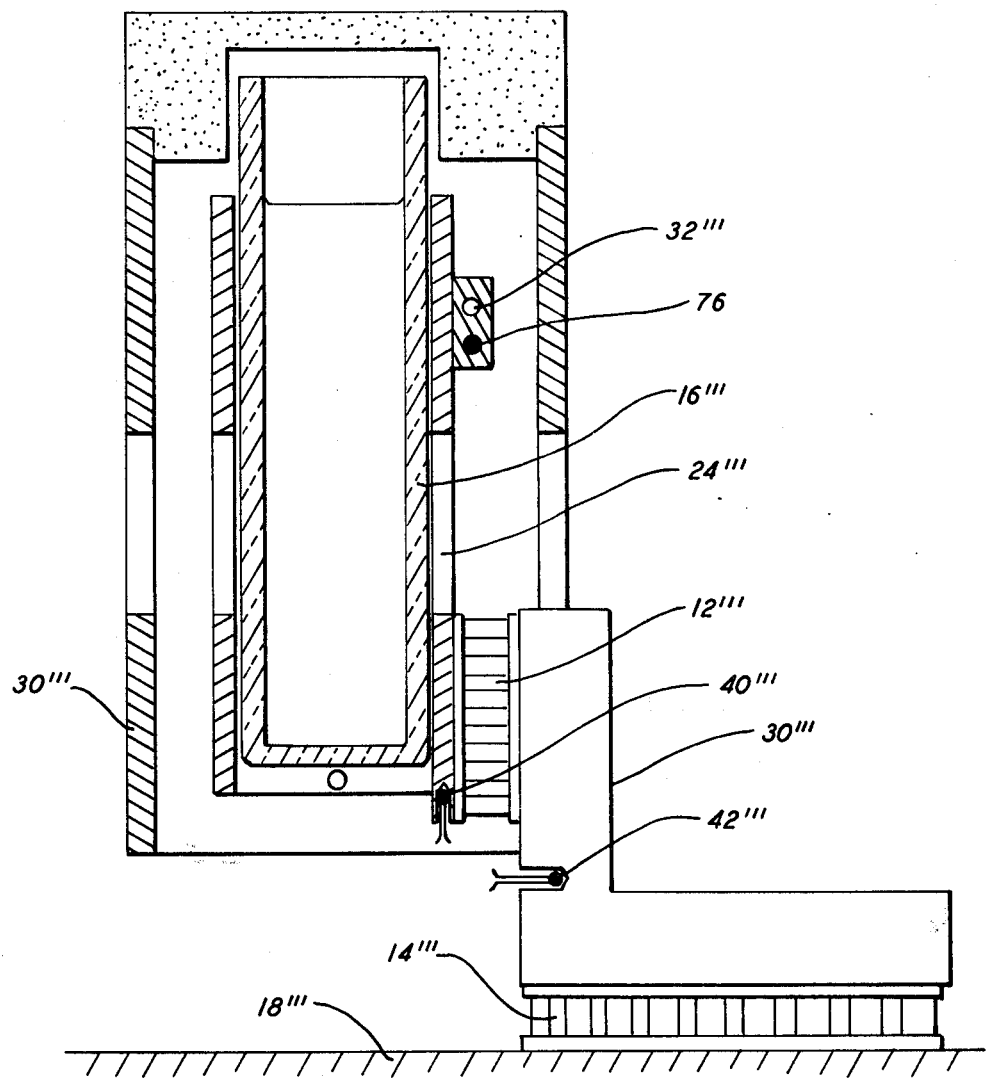
FIG. 7 illustrates a further embodiment of this invention wherein a modification to minimize overshooting is incorporated.

With some loss in temperature accuracy the inconvenience of an immersed sensor can be avoided. Instead of a well for the temperature sensor 32' (FIG. 4) can be provided in the thermal contact bar 24' (as shown in FIG. 6) to prevent the thermal runaway of the Peltier units 12' and 14'. Of course, if an immersed sensor is desireable, by placing the temperature sensor 32' in this well when the cuvette 16' is removed, the temperature control apparatus of FIG. 4 would maintain the thermal contact bar 24' at the set temperature and thermal runaway would be thereby avoided. Furthermore, a liner 74 presenting the same thermal lag as the wall of the cuvette 16' may be provided within this well so that the temperature sensor 32' can be permanently disposed therein to track the temperature of the sample, as shown in FIG. 6. The thermal contact bar 24''' may be extended to completely surround the cuvette 16''' where the reponse time to stabilization at the temperature set point may be compromised. This embodiment is shown in FIG. 7. As shown is this form the temperature sensor 32''' could be permanently located without a liner being required externally on the wall of the extended thermal contact member 24''' at a point best representing cuvette temperature, usually near the top.

The extent of overshoot which results from slewing to the temperature set point in either thermal direction depends on the thermal gradient which exists between the thermal contact bar 24' (FIG. 4) and the cuvette 16' at the time when the temperature sensor 32' detects that the temperature set point has been reached. In the configuration of FIG. 7 the greater mass of the contact member 24''' augments overshoot. To reduce this overshoot without increasing the thermal response time, a set point antcipation feature can be accomplished by thermally disposing another thermistor 76 in the thermal contact member 24''' of FIG. 7 to track the temperature of the sample and series connecting this thermistor with another resistor 78 in the bridge circuitry of FIG. 3. A comparator 80 is included as part of this anticipation feature in the circuitry of FIG. 3, with the inputs thereof connected respectively to the bridge circuit point 62 or an equivalent voltage and the bridge circuit point between resistor 78 and thermistor 76. Although not shown in FIG. 3, the output from comparator 80 is connected in the additive sense to the input of comparator 36' to which output from the bridge circuit 34' with the temperature sensor 32' therein is connected. Because the output from comparator 80 is proportional to the thermal gradient across cuvette 16''' as represented by the temperature difference between thermistors 40''' and 76, the output from comparator 36' that controls Peltier unit 12''' includes components that are proportional to the gradient across the cuvette 16''' and to the deviation from the set point of the sample temperature respectively. As these components are additive Peltier 12''' shuts-off before the set point is reached to reduce the thermal overshoot encountered. As the gradient then decays as the temperature of the thermal contact member approaches the set temperature the set point anticipation feature functions to bring the sample temperature to set point with little or no overshoot. We have found this anticipation circuit to be so effective that the stirrer can be omitted without overshoot resulting from the increased thermal lag.

Those skilled in the art will understand that the present disclosure has been made by way of example and that numerous changes in the details of construction and the combination or arrangement of parts may be resorted to without departing from the true spirit and the scope of this invention. Therefore, the present disclosure should be construed as illustrative rather than limiting.

What I claim is:

1. Apparatus for controlling the temperature of a specimen, comprising:
    a first Peltier unit having first and second thermal junctions, said first thermal junction thereof being interfaced with the specimen;
    a second Peltier unit having first and second thermal junctions, said first thermal junction thereof being interfaced with said second thermal junction of said first Peltier, said second thermal junction thereof being interfaced with an ambient heat sink;
    means for controlling the power to said first Peltier unit in proportion to the temperature differential between the specimen and a set point; and
    means for controlling the power to said second Peltier in proportion to the temperature differential across said first Peltier.

2. The apparatus of claim 1 wherein output from said second Peltier control means is applied to offset said set point of said first Peltier control means in compensating for thermal losses to ambient.

3. The apparatus of claim 1 wherein said second Peltier control means includes first and second thermistors interconnected in a single bridge circuit with a pair of interconnected resistors, said bridge circuit having the output from an operational amplifier applied at the bridge circuit point between said resistors and the bridge circuit point between one thermistor and one resistor connecting at one input of said operational amplifier, the other input of said operational amplifier connecting with a fixed voltage relative to the bridge circuit point between said thermistors, the sensitivity of said bridge circuit thereby being substantially independent of the temperature sensed by said thermistor at the input of said operational amplifier.

4. The apparatus of claim 3 wherein output from at least one of said Peltier control means is grounded through an FET switch having the gate thereof connected to the output from a comparator, said bridge circuit point between said resistors connecting to one input of said comaprator and the other input thereof connecting to a fixed voltage relative to the bridge circuit point between said thermistors, said Peltier units being thereby shut-off when said thermistor at the input of said operational amplifier reaches a predetermined temperature.

5. The apparatus of claim 3 wherein a third thermistor and a third resistor are interconnected in said bridge circuit with all of said thermistors connecting at one common bridge circuit point and with all of said resistors connecting at another common bridge circuit point, the bridge circuit point between said third resistor and said third thermistor connecting to one input of a comparator and the other input thereof connecting to the bridge circuit point between said thermistor and said resistor, the output of said comparator being so connected to said first control means that said first Peltier unit is thereby shut off before said set point of said first Peltier control means is reached to reduce thermal overshoot.

6. The apparatus of claim 1 wherein the specimen is a flow cell in a spectrophotometer with a first and a second sensor means disposed therein for developing an electrical signal in proportion to temperature at locations adjacent to the passage through the flow cell and said first Peltier unit respectively, while a heat sink thermally interfaces between said first and second Peltier units with a third sensor means disposed therein adjacent to said first Peltier unit for developing an electrical signal in proportion to temperature; and wherein said first Peltier control means includes a first comparator having the signal from said first sensor means connected to one input thereof and means for establishing a variable set point connected to the other input thereof with output therefrom connecting to drive said first Peltier unit, while said second Peltier control means includes a second comparator having the signal from said second sensor means connected to one input thereof and the signal from said third sensor means connected to the other input thereof with output therefrom connecting to drive said second Peltier unit.

7. The apparatus of claim 1 wherein the specimen is at least one cuvette in a cuvette basket of a spectrophotometer with a first sensor means immersed in the sample contained by the cuvette for developing an electrical signal in proportion to temperature and a thermal contact bar interfaces between the cuvettes and said first Peltier unit with a second sensor means disposed therein adjacent to said first Peltier unit for developing an electrical signal in proportion to temperatue, while said cuvette basket thermally interfaces between said first and second Peltier units with a third sensor means disposed therein adjacent to said first Peltier unit for developing an electrical signal in proportion to temperature; and wherein said first Peltier control means includes a first comparator having the signal from said first sensor means connected to one input thereof and means for establishing a variable set point connected to the other input thereof with output therefrom connecting to drive said first Peltier unit, while said second Peltier control means includes a second comparator having the signal from said second sensor means connected to one input thereof and the signal from said third sensor means connected to the other input thereof with output therefrom connecting to drive said second Peltier unit.

8. The apparatus of claim 1 wherein the specimen is at least one cuvette in a cuvette basket of a spectrophotometer and a thermal contact bar interfaces between the cuvettes and said first Peltier unit with a first and a second sensor means disposed therein for developing an electrical signal in proportion to temperature, while said cuvette basket thermally interfaces between said first and second Peltier units with a third sensor means disposed therein adjacent to said first Peltier unit for developing an electrical signal in proportion to temperature, said second sensor means being located adjacent to said first Peltier unit; and wherein said first Peltier control means includes a first comparator having the signal from said first sensor means connected to one input thereof and means for establishing a variable set point connected to the other input thereof with output therefrom connecting to drive said first Peltier unit, while said second Peltier control means includes a second comparator having the signal from said second sensor means connected to one input thereof and the signal from said third sensor means connected to the other input thereof with output therefrom connecting to drive said second Peltier unit.

9. The apparatus of claim 1 wherein the specimen is at least one cuvette in a cuvette basket of a spectrophotometer and a thermal contact bar interfaces between the sample contained in the cuvette and said first Peltier unit with a first and a second sensor means disposed therein for developing an electrical signal in proportion to temperature at locations adjacent to the sample and said first Peltier unit respectively, while said cuvette basket thermally interfaces between said first and second Peltier units with a third sensor means disposed therein adjacent to said first Peltier unit for developing and electrical signal in proportion to temperature; and wherein said first Peltier control means includes a first comparator having the signal from said first sensor means connected to input thereof and means for establishing a variable set point connected to the other input thereof with output therefrom connecting to drive said first Peltier unit, while said second Peltier control means includes a second comparator having the signal from said second sensor means connected to one input thereof and the signal from said third sensor means connected to the other input thereof with output therefrom connecting to drive said second Peltier unit.

* * * * *